US006862915B2

(12) United States Patent
Staphanos et al.

(10) Patent No.: US 6,862,915 B2
(45) Date of Patent: Mar. 8, 2005

(54) OXYGEN ANALYZER WITH ENHANCED CALIBRATION AND BLOW-BACK

(75) Inventors: Stephen T. Staphanos, Long Beach, CA (US); Marion A. Keyes, St. Louis, MO (US)

(73) Assignee: Rosemount Analytical Inc., Anaheim, CA (US)

( * ) Notice: Subject to any disclaimer, the term of this patent is extended or adjusted under 35 U.S.C. 154(b) by 0 days.

(21) Appl. No.: 10/393,378

(22) Filed: Mar. 20, 2003

(65) Prior Publication Data

US 2004/0182133 A1 Sep. 23, 2004

(51) Int. Cl.[7] .......................................... G01N 33/497
(52) U.S. Cl. ...................................... 73/23.31; 73/23.2
(58) Field of Search ................................ 73/23.31, 23.2

(56) References Cited

U.S. PATENT DOCUMENTS

| | | | |
|---|---|---|---|
| 3,559,491 A | 2/1971 | Thoen ........................ 73/421.5 |
| 3,928,161 A | 12/1975 | McIntyre et al. ........... 204/195 |
| 4,094,187 A | * 6/1978 | Navarre, Jr. .............. 73/863.83 |
| 4,161,883 A | 7/1979 | Laird et al. ................ 73/421.5 |
| 4,247,380 A | 1/1981 | McIntyre .................... 204/195 |
| 4,284,487 A | 8/1981 | Barnes et al. ............... 204/195 |
| 4,496,433 A | * 1/1985 | Annino et al. .............. 205/784 |
| 4,560,873 A | * 12/1985 | McGowan et al. .... 250/339.09 |
| 4,578,986 A | * 4/1986 | Navarre ....................... 73/61.59 |
| 4,601,882 A | * 7/1986 | Benner ......................... 422/80 |
| 5,178,022 A | 1/1993 | Tomlin ..................... 73/864.81 |
| 5,184,017 A | * 2/1993 | Tury et al. ................... 250/343 |
| 5,376,163 A | * 12/1994 | Carlson et al. ................ 95/22 |
| 5,507,192 A | 4/1996 | Beaudin .................. 73/863.33 |
| 5,993,623 A | 11/1999 | O'Neill et al. .............. 204/424 |
| 6,092,430 A | * 7/2000 | Liston et al. ............. 73/863.81 |
| 6,114,700 A | * 9/2000 | Blades ........................ 250/343 |
| 6,120,664 A | 9/2000 | Patel et al. ................. 204/428 |
| 6,200,819 B1 | 3/2001 | Harvey et al. .............. 436/179 |
| 6,701,255 B2 | * 3/2004 | Batug et al. ................... 702/24 |
| 2003/0216660 A1 | * 11/2003 | Ben-Oren et al. .......... 600/532 |
| 2004/0074279 A1 | * 4/2004 | Forrest ........................ 73/1.06 |

FOREIGN PATENT DOCUMENTS

| | | |
|---|---|---|
| EP | 0 909 942 | 4/1999 |
| JP | 07-260740 | 10/1995 |
| JP | 2000-171358 | 6/2000 |
| WO | WO 87/01453 | 3/1987 |
| WO | WO 98/13687 | 4/1998 |

* cited by examiner

Primary Examiner—Hezron Williams
Assistant Examiner—Rodney Frank
(74) Attorney, Agent, or Firm—Westman, Champlin & Kelly, P.A.

(57) ABSTRACT

A combustion gas analyzer for measuring the concentration of a gas constituent in an exhaust gas stream is provided. The gas analyzer includes a sensor cell assembly coupled to a transmitter having electrical circuitry configured to provide an output of the concentration of the gas constituent as sensed by the sensor cell assembly. The combustion gas analyzer also includes a filter substantially enclosing the sensor cell assembly and a conduit coupled to the filter at a first end of the conduit and coupled to a valve assembly at a second end of the conduit. The conduit is used for supplying a calibration gas to the sensor cell assembly or for supplying a blow-back gas used to purge the filter.

21 Claims, 5 Drawing Sheets

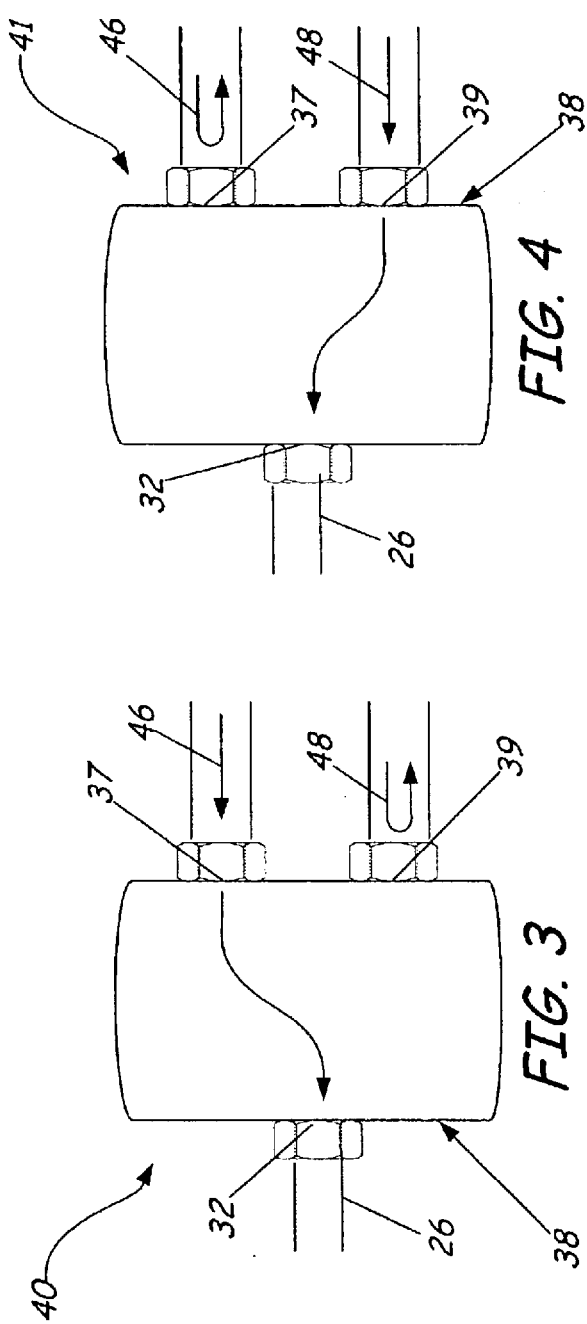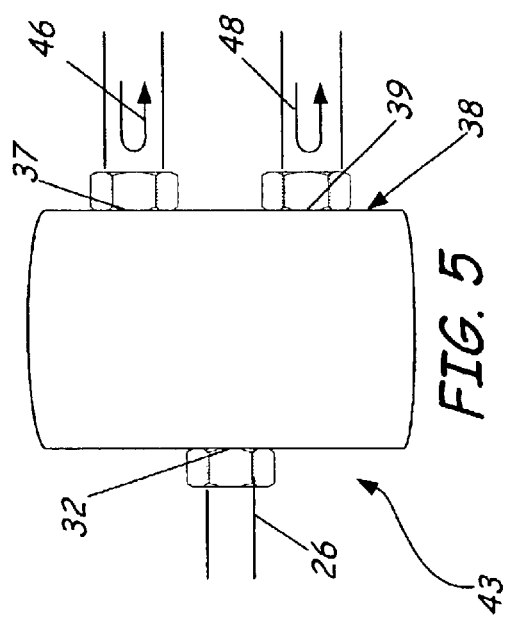

OXYGEN ANALYZER WITH ENHANCED CALIBRATION AND BLOW-BACK

BACKGROUND OF THE INVENTION

The present invention relates generally to the field of gas analysis instrumentation, and more specifically to a combustion gas analyzer.

Industrial processes are used in the manufacture or combustion of various materials. It is often desirable to monitor operation of a process such that the process can be controlled and adjusted accordingly. Exhaust gas from the combustion is vented through a stack.

Combustion analyzers are used to measure the concentrations of a variety of exhaust gases in industrial combustion processes. For example, the exhaust gas in a combustion process consists of by-product and excess gases. The concentrations of exhaust gases, such as oxygen, oxides of nitrogen, sulfur dioxide and carbon monoxide, relate to the combustion efficiency of the process. Exhaust gas concentration measurements enable operators to adjust the amount of fuel supplied to the process to attain an efficient combustion.

Combustion oxygen analyzers are designed to measure the net concentration of excess oxygen in a combustion process. Excess oxygen is the oxygen remaining after all oxygen has been oxidized in the process and is related to the efficiency of the combustion process. An example of such a device is the Oxymitter 4000 manufactured and sold by Rosemount Analytical, Inc. of Orrville, Ohio. Common applications for a combustion oxygen analyzer include: glass furnaces, coking ovens, catalytic crackers, utility coal pulverizers, sulfur paint incinerators, and other industrial incinerators.

The combustion oxygen analyzer includes a sensor cell assembly which is positioned within an exhaust stack or duct which vents the exhaust gas from a combustion chamber. The sensor cell assembly includes a diffusion element and a sensing cell. As the exhaust gas is vented through the stack, it enters the sensor cell assembly and the diffusion element disperses the gas about the sensing cell. An electrical output from the sensor cell is indicative of oxygen concentration. Electrical circuitry in the transmitter reads the sensor cell output and provides an output related to oxygen concentration.

The combustion oxygen analyzer must be periodically calibrated in order to maintain accuracy in measurements. For example, the sensitivity of the sensor cell can drift over time. Calibration is through a process of standardizing the analyzer by determining the deviation between actual oxygen concentration and measured oxygen concentration. The deviation is used to adjust the output of the analyzer to bring it back into calibration. For example, to calibrate an oxygen analyzer, a calibration gas containing a mixture of oxygen and other gases has a known concentration of oxygen and is applied to the sensor cell assembly. The sensor cell assembly senses the concentration of oxygen in the calibration gas. The electrical circuitry provides an output value for the measured oxygen concentration. The measured value of oxygen is compared to the known concentration of oxygen in the calibration gas. A correction factor is calculated and can be applied to all subsequent measurements of the exhaust gas until a future calibration is performed. The correction factor can be stored, for example, in a memory in the transmitter.

In another calibration technique, the electrical circuitry in the transmitter measures impedance of the sensing cell to provide an indication of the accuracy of the sensing cell. An indication that the sensing cell is inaccurate can be used to indicate that calibration is required.

The calibration process typically requires the process to be shut down so that the analyzer can be removed from the stack for application of the calibration gas. Further, in applications where exhaust gas contains a high particle content, the diffusion element can become plugged and damaged. This also requires the industrial process to be shut down so that the diffusion element can be cleaned or replaced. Diffusion element maintenance and other procedures requiring the sensor cell assembly to be removed from service are time consuming and costly.

SUMMARY OF THE INVENTION

A combustion gas analyzer for measuring the concentration of a gas constituent in an exhaust gas stream includes a sensor cell assembly which is configured to sense the gas constituent. A filter substantially encloses the sensor cell assembly. A valve assembly is coupled to a conduit which connects to the filter. The conduit is used for supplying a calibration gas or for back washing dust particles in the filter.

BRIEF DESCRIPTION OF THE DRAWINGS

FIG. 3 is an expanded view of the valve assembly in accordance with an embodiment of the present invention.

FIG. 4 is an expanded view of the valve assembly in accordance with an embodiment of the present invention.

FIG. 5 is an expanded view of the valve assembly in accordance with an embodiment of the present invention.

DETAILED DESCRIPTION OF THE PREFERRED EMBODIMENTS

Figure 1:
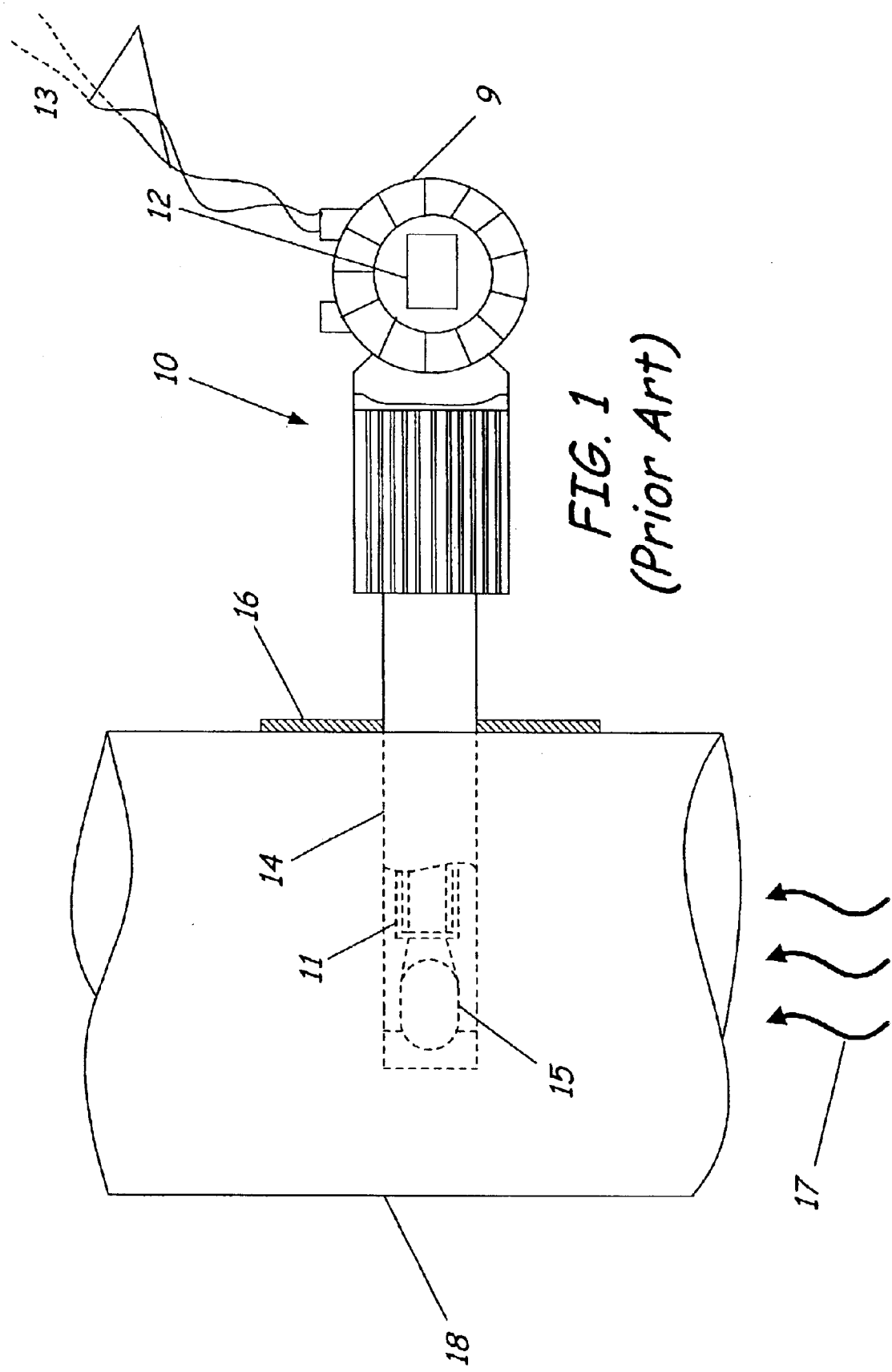
FIG. 1 shows a combustion gas analyzer mounted on a stack in accordance with the prior art.

FIG. 1 depicts gas analyzer 10 which is used to measure the concentration of gases in exhaust gas 17. The exhaust gas 17 is vented through stack 18 from an industrial process. Measured concentration of gas, such as oxygen, oxides of nitrogen, sulfur dioxide and carbon monoxide, in exhaust gas 17 relate to the combustion efficiency of the industrial process. The amount of fuel supplied to the industrial process can be adjusted to attain efficient combustion based upon the concentration of the gases in exhaust gas 17.

Gas analyzer 10 includes sensor cell assembly 14 positioned and supported in stack 18 by flange 16. Stack 18 is a flue or duct of an industrial combustion process and carries exhaust gas 17. Sensor cell assembly 14 includes a diffusion element 15 and sensing cell 11. Diffusion element 15 disperses exhaust gas 17 about the sensing cell 11 as exhaust gas 17 enters the sensor cell assembly 14. Electrical circuitry 12 in transmitter 9 is coupled to and reads an electrical output from the sensor cell 11 indicative of gas concentration. Electrical circuitry 12 provides gas concentration output through output conductors 13.

If there is a high particle content in exhaust gas 17, the diffusion element 15 can become plugged and damaged. To replace diffusion element 15, the industrial process must be shut down so that diffusion element 15 can be cleaned or replaced. As a result of a high particle content in exhaust gas 17, cleaning or replacing diffusion element 15 is time consuming and costly. Further, as discussed in the Background section, the gas analyzer 10 may need to be removed from the stack for calibrating.

Figure 2:
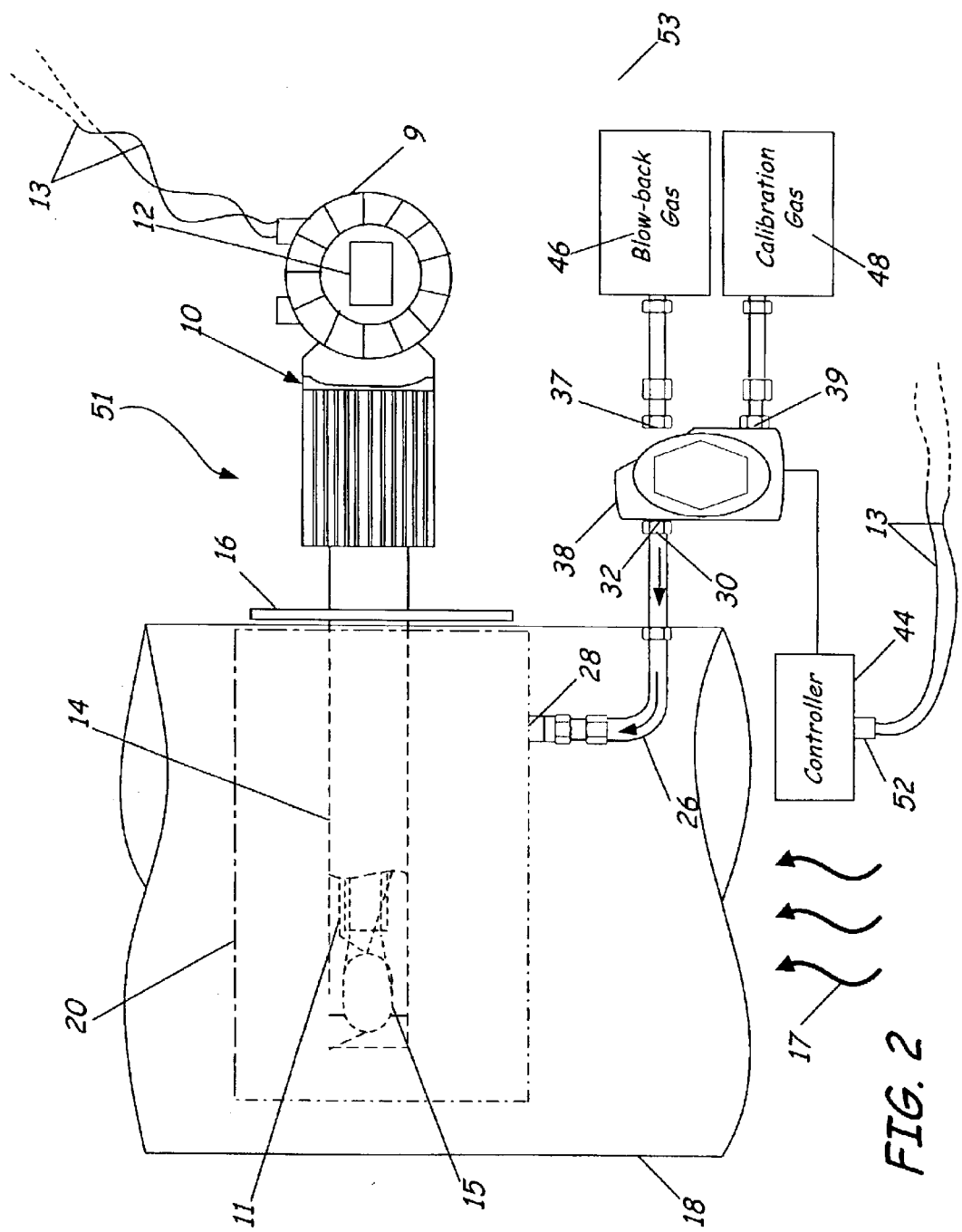
FIG. 2 is a combustion gas analyzer system mounted on a stack in accordance with an embodiment of the present invention.

FIG. 2 depicts gas analyzer system 51 in accordance with an embodiment of the present invention. Gas analyzer system 51 includes filter 20. For example filter 20 can be a porous metal filter such as those available from Mott Corporation of Farmington, Conn. Filter 20 encloses sensor cell assembly 14 and traps particulate matter in exhaust gas 17 as exhaust gas 17 moves past sensor cell assembly 14. Filter 20 prevents particulate matter from reaching sensor cell assembly 14.

Gas analyzer system 51 also includes valve assembly 38 coupled to filter 20 by a conduit 26. Conduit 26 is approximately 0.25 inches in diameter in this example and has a first end 28 connected to filter 20 and a second end 30 connected to an outlet port 32 of valve assembly 38. Conduit 26 can be of any appropriate length such that valve assembly 38 can be positioned at the base of stack 18 where an operator can easily reach it. Valve assembly 38 also includes first inlet port 37 and second inlet port 39 as discussed below.

As filter 20 traps particulate matter in exhaust gas 17, filter 20 may become plugged and prevent a sufficient amount of exhaust gas 17 from entering the sensor cell assembly 14. One technique to clean filter 20 is to shut down the industrial process and clean or replace filter 20 in the stack. This technique of cleaning or replacing filter 20 is time consuming and costly. Therefore, in one aspect of the invention, gas analyzer system 51 includes a blow-back operation to periodically purge and dislodge particulate matter in filter 20.

First inlet port 37 of valve assembly 38 is coupled to pressurized blow-back gas 46 which is set, for example, to more then 10 psig higher than the industrial process. When filter 20 becomes plugged with trapped particulate matter, pressurized blow-back gas 46 is directed from first inlet 37 of valve assembly 38 to exit outlet port 32 through valve assembly 38. Valve assembly 38 can be manually operated, operated by gas analyzer 10 or operated by another controller such as controller 44. Pressurized blow-back gas 46 travels through conduit 26 and enters filter 20. For example, when gas analyzer 10 is a combustion oxygen analyzer, pressurized blow-back gas 46 can consist of dry pressurized air or dry pressurized nitrogen.

In another aspect of the invention, gas analyzer 10 must be periodically calibrated in order to maintain accuracy in gas concentration measurements. Gas analyzer system 51 includes a calibration operation. Gas analyzer 10 is calibrated using calibration gas 48. Second inlet port 39 is coupled to the pressurized calibration gas 48 which is at least 10 psig higher than the industrial process. Valve assembly 38 is operated to allow pressurized calibration gas 48 to enter second inlet 39 of valve assembly 38 and exit outlet port 32. Valve assembly 38 can be manually operated, operated by gas analyzer 10 or operated by another controller such as controller 44. Pressurized calibration gas 46 travels through conduit 26 and floods sensor cell assembly 14. When gas analyzer 10 is a combustion oxygen analyzer, pressurized calibration gas 48 consists of, for example, a mixture of nitrogen and a known concentration of oxygen.

During the calibration process, sensor cell assembly 14 senses the concentration of oxygen in the calibration gas 48. The electrical circuitry 12 provides an output value representative of the measured oxygen concentration. The measured value of oxygen concentration is compared to the known concentration of oxygen in the calibration gas 48. A correction factor is calculated and can be applied to all subsequent measurements of the exhaust gas 17 until a future calibration is performed. The correction factor can be stored, for example, in a memory in transmitter 9.

The particular implementation of valve assembly 38 can be configured as desired. FIGS. 3–5 are diagrams which show three example configurations for valve assembly 38 when manually operated, operated by gas analyzer 10 or operated by a controller such as controller 44. In FIG. 3, first inlet port 37 is coupled to outlet port 32 when valve assembly 38 is in a first position 40. First position 40 allows pressurized blow-back gas 46 to flow through conduit 26 and into filter 20 to purge filter 20 of particulate matter. In FIG. 4, second inlet port 39 is coupled to outlet port 32 when valve assembly 38 is in a second position 41. Second position 41 also allows pressurized calibration gas 48 to flow through conduit 26 and flood sensor cell assembly 14 to calibrate the sensing cell 11. In FIG. 5, valve assembly 38 is in a third position 43 in which neither first inlet port 37 nor second inlet port 39 are coupled to outlet port 32. Both blow-back gas 46 and calibration gas 48 are blocked from flowing through conduit 26 in third position 43.

Regardless if the operation is manually operated, operated by gas analyzer 10 or oeprated by controller 44, each position of valve assembly 38 relates to whether gas analyzer system 51 is purging filter 20, calibrating the sensor cell 11, or doing neither.

Referring back to FIG. 2, when valve assembly 38 is operated by controller 44, controller 44 includes input 52. In some embodiments of the invention, input 52 is coupled to transmitter 9 through conductors 13. Electrical circuitry 12, in this configuration, measures impedance of the sensing cell 11 to determine if sensing cell 11 is drifting in accuracy. When the measured impedance indicates an inaccuracy of the sensing cell 11, a signal is transmitted through conductor 13 to input 52. This signal indicates that a calibration operation should be initiated. Electrical circuitry 12 can monitor response speed of sensing cell 11 during the application of calibration gas 48 and exhaust gas 17. A slow response speed can be an indicator that the filter 20 is clogged. When a slow response speed is detected, controller 44 can initiate a blow-back operation.

In other embodiments of the invention, valve assembly 38 is controlled by controller 44 which stores, for example in a memory of controller 44, pre-programmed time intervals conveyed through input 52. In this configuration, a clock periodically initiates valve assembly 38 to perform the blow-back operation or the calibration operation.

In other embodiments of the invention, controller 44 has a user input 52. In this configuration, input 52 receives a signal from an operator to initiate either a blow-back or calibration operation.

All and/or some of all the above-identified inputs can be included in controller 44. Controller 44 can be a programmable logic controller (PLC), digital controller (DC), a pneumatic controller or any other process controller or comparable device.

Figure 6:
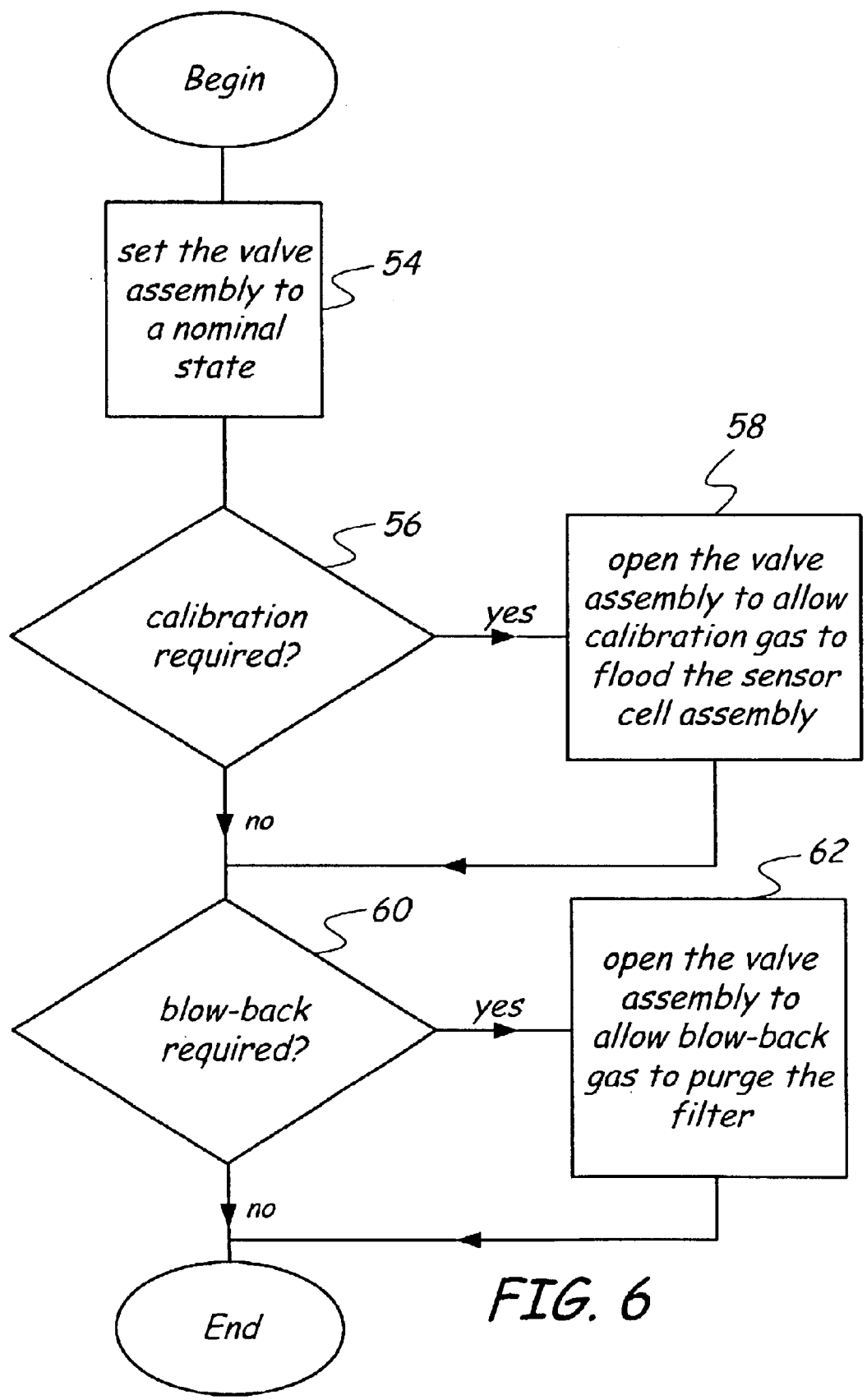
FIG. 6 is a flow diagram showing a method of a controller operating a valve assembly in accordance with an embodiment of the present invention.

FIG. 6 is a flow diagram which shows an example of a method with which controller 44 operates valve assembly 38. The method begins at first step 54 where controller 44 sets valve assembly 38 in a nominal state. In the nominal state, calibration gas 48 and blow-back gas 46 are blocked from flowing through conduit 26.

At step 56, controller 44 determines whether a calibration is required. If a calibration is required, the process advances to step 58. At step 58, the controller opens the valve assembly 38 to allow calibration gas 48 to flood the sensor cell assembly 14. After calibration gas 48 is allowed to flood the sensor cell assembly 14, the process passes control to step 60. If a calibration is not required in step 56 the process passes control to step 60.

At step 60, controller 44 determines whether a blow-back is required. If a blow-back is required, the process advances to step 62. At step 62, controller 44 opens the valve assembly 38 to allow blow-back gas 46 to purge filter 20. After blow-back gas 46 is allowed to purge filter 20, the method ends. If a blow-back is not required in step 60 the method also ends.

Figure 7:
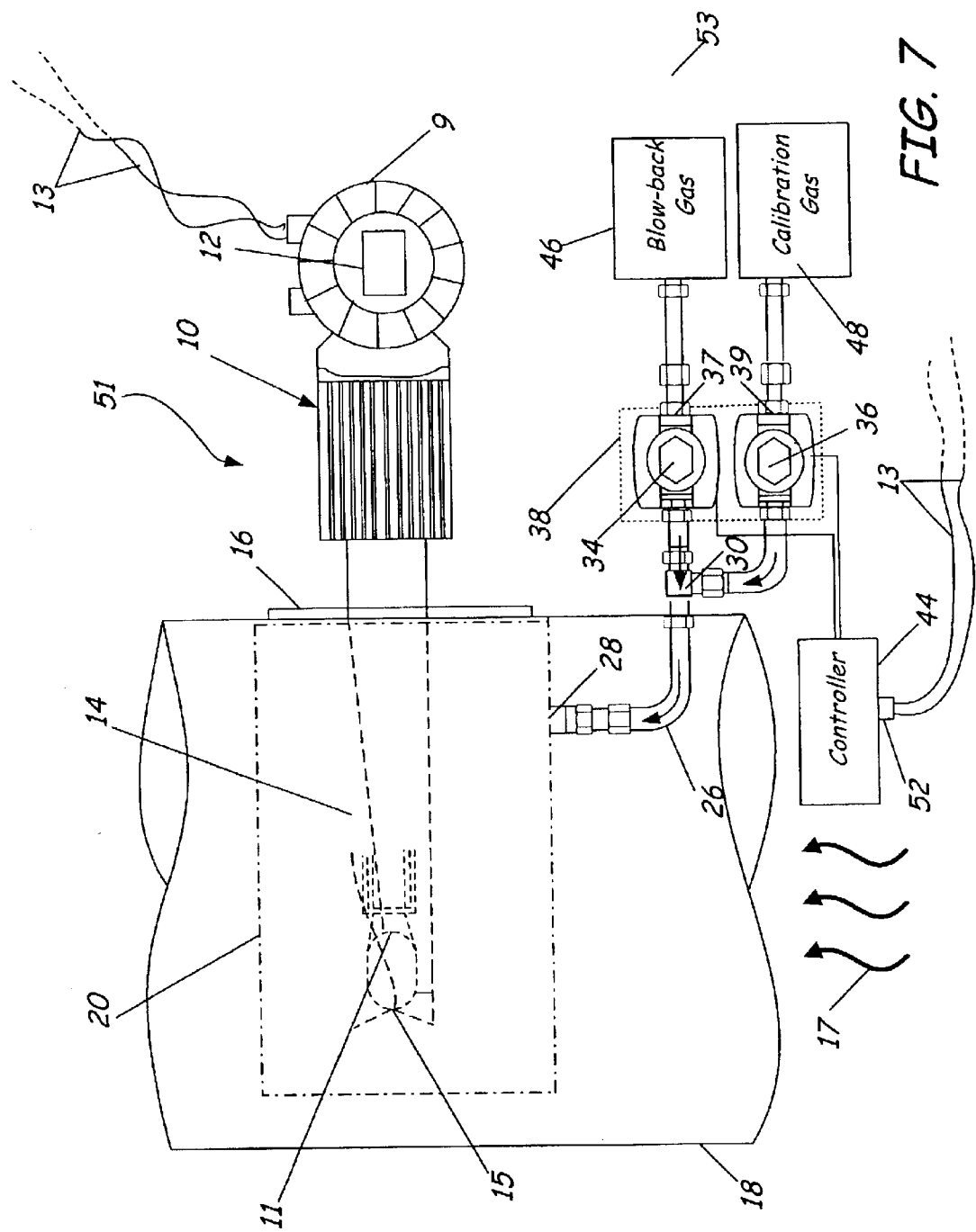
FIG. 7 is a combustion gas analyzer system mounted on a stack in accordance with another embodiment of the present invention.

FIG. 7 depicts gas analyzer system 51 in accordance with another aspect of the present invention. Valve assembly 38 includes first solenoid valve 34 and second solenoid valve 36. For example, solenoid valves 34 and 36 can be two-way solenoid valves, three-way solenoid valves, and four-way solenoid valves. Solenoid valves 34 and 36 can be manually operated, operated by gas analyzer 10 or operated by controller 44 as in the method previously discussed.

When solenoid valve 34 is open and solenoid valve 36 remains closed, pressurized blow-back gas 46 is allowed to flow through conduit 26 and purge filter 20 as discussed above. When solenoid valve 36 is open and solenoid valve 34 remains closed, pressurized calibration gas 48 is allowed to flow through conduit 26 and flood sensor cell assembly 14 to calibrate the sensor cell 11 as discussed above. Lastly, when solenoid valves 34 and 36 are both closed, blow-back gas 46 and calibration gas 48 are blocked from flowing through conduit 26.

Although the present invention has been described with reference to preferred embodiments, workers skilled in the art will recognize that changes may be made in form and detail without departing from the spirit and scope of the invention.

What is claimed is:

1. An apparatus for measuring the concentration of a gas constituent in a combustion exhaust gas stream the apparatus comprising;
   a sensor cell assembly configured to be positioned within a process stack and configured to sense the gas constituent;
   a transmitter having electrical circuitry coupled to the sensor cell assembly and configured to provide an output related to the concentration of the gas constituent;
   a filter disposed about the sensor cell assembly;
   a conduit having a first end coupled to the filter and a second end; and
   a valve assembly including a valve coupled to the second end of the conduit configured to selectively apply a pressurized gas to the filter through the conduit.

2. The apparatus of claim 1, wherein the filter comprises porous metal.

3. The apparatus of claim 1, wherein the valve assembly is operated by a controller.

4. The apparatus of claim 3, wherein the controller is automated.

5. The apparatus of claim 1, wherein the valve assembly is manually operated.

6. The apparatus of claim 1, wherein the valve assembly is operated by the transmitter.

7. The apparatus of claim 1, wherein the valve assembly further comprises:
   a first inlet coupled to an outlet when the valve assembly is in a first position;
   a second inlet coupled to the outlet when the valve assembly is in a second position; and
   wherein the valve assembly is configured such that when the valve assembly remains closed the valve assembly is in a third position and neither of the first and second inlets are coupled to the outlet.

8. The apparatus of claim 7, wherein when the valve assembly is in the first position a pressurized blow-back gas is allowed to flow through the conduit to the filter.

9. The apparatus of claim 7, wherein when the valve assembly is in the second position a pressurized calibration gas is allowed to flow through the conduit to the sensor cell assembly.

10. The apparatus of claim 7, wherein when the valve assembly is in the third position a pressurized blow-back gas and a pressurized calibration gas are blocked from flowing through the conduit.

11. The apparatus of claim 1, wherein the valve assembly comprises a first solenoid valve and a second solenoid valve.

12. The apparatus of claim 11, wherein the first solenoid valve and the second solenoid valve are selected from the group consisting of two-way solenoid valves, three-way solenoid valves and four-way solenoid valves.

13. The apparatus of claim 11, wherein the first solenoid valve is configured to allow the flow of a pressurized blow-back gas through the conduit to the filter when the first solenoid valve is open.

14. The apparatus of claim 11, wherein the second solenoid valve is configured to allow the flow of a pressurized calibration gas through the conduit to the sensor cell assembly when the second solenoid valve is open.

15. A method of maintaining a sensor cell assembly in a combustion gas analyzer, the method comprising:
   providing a filter disposed about the sensor cell assembly to filter particulate in an exhaust gas stream;
   providing a valve assembly coupled to the filter by a conduit;
   supplying a pressurized blow-back gas for dislodging trapped particulate in the filter through the conduit;
   supplying a pressurized calibration gas to calibrate the sensor cell assembly through the conduit; and
   controlling the supplying of the pressurized blow-back gas and the calibration gas with the valve assembly.

16. The method of claim 15, wherein providing the valve assembly further comprises:
   providing a first inlet coupled to an outlet for periodically allowing the supplying of the pressurized blow-back gas through the conduit to the filter; and
   providing a second inlet coupled to the outlet for periodically allowing the supplying of the pressurized calibration gas through the conduit to the sensor cell assembly.

17. The method of claim 15, wherein providing the valve assembly further comprises:
   providing a first solenoid valve for periodically allowing the pressurized blow-back gas through the conduit to the filter; and
   providing a second solenoid valve for periodically allowing the pressurized calibration gas through the conduit to the sensor cell assembly.

18. The method of claim 15, wherein regulating the valve assembly further comprises:

setting the valve assembly in a nominal state, wherein the nominal state blocks the pressurized blow-back gas and the pressurized calibration gas from flowing through the conduit; and periodically opening the valve assembly to release one of the pressurized blow-back gas and the pressurized calibration gas.

19. A method of measuring the concentration of a gas constituent in a combustion exhaust gas stream, the method comprising:

providing a conduit having a first end couple to a filter and a second end;

providing a valve assembly including a valve coupled to the second end of the conduit configured to selectively apply a pressurized gas to the filter through the conduit;

sensing a gas constituent with a sensor cell assembly disposed within the filter; and providing an output related to the concentration of the gas constituent.

20. The method of claim 19, wherein providing a valve assembly further comprises:

providing a first inlet couple to an outlet when the valve assembly is in a first position, the first position directing a pressurized blow-back gas through the conduit to purge the filter;

providing a second inlet coupled to the outlet when the valve assembly is in a second position, the second position directing a pressurized calibration gas through the conduit to flood the sensor cell assembly; and wherein providing the valve assembly is configured such that when the valve assembly in a third position the valve assembly blocks the pressurized blow-back gas and the pressurized calibration gas from being directed through the conduit.

21. The method of claim 19, wherein providing the valve assembly further comprises:

providing a first solenoid valve configured to periodically direct the flow of a pressurized blow-back gas through the conduit to purge the filter when the first solenoid valve is open; and providing a second solenoid valve configured to periodically direct the flow of a pressurized calibration gas through the conduit to flood the sensor cell assembly when the second solenoid valve is open.

* * * * *